United States Patent [19]

Kanakkanatt

[11] Patent Number: 5,501,945
[45] Date of Patent: Mar. 26, 1996

[54] METHOD OF USING MULTICHROMIC POLYMERS IN PACKAGING

[75] Inventor: Sebastian V. Kanakkanatt, Akron, Ohio

[73] Assignee: The University of Akron, Akron, Ohio

[21] Appl. No.: 298,465

[22] Filed: Aug. 30, 1994

[51] Int. Cl.⁶ ............................ B65B 55/00; G03C 1/73; A23L 3/00; A61L 2/00
[52] U.S. Cl. .................. 430/338; 430/345; 523/100; 426/323; 426/415
[58] Field of Search .................. 523/100; 426/323, 426/544, 545, 331, 415; 430/338, 345

[56] References Cited

U.S. PATENT DOCUMENTS

| | | | |
|---|---|---|---|
| 3,341,330 | 9/1967 | Foris | 430/17 |
| 3,346,385 | 10/1967 | Foris | 430/275 |
| 3,355,293 | 11/1967 | Foris | 430/17 |
| 3,660,094 | 5/1972 | Poot | 430/345 |
| 3,773,508 | 11/1973 | Osada et al. | 430/337 |
| 3,785,820 | 1/1974 | Inoue et al. | 430/19 |
| 3,847,611 | 11/1974 | Van Royen et al. | 430/334 |
| 4,010,033 | 3/1977 | Metzger | 430/334 |
| 4,171,980 | 10/1979 | Ceintrey | 427/145 |
| 4,237,207 | 12/1980 | Ceintrey | 430/17 |
| 4,758,547 | 7/1988 | Itabashi et al. | 503/207 |
| 4,842,981 | 6/1989 | Sanders et al. | 430/345 |
| 5,206,118 | 4/1993 | Sidney et al. | 430/338 |
| 5,208,132 | 5/1993 | Kamada et al. | 430/338 |
| 5,289,547 | 2/1994 | Ligas et al. | 382/7 |
| 5,371,058 | 12/1994 | Wittig, Jr. et al. | 503/206 |

FOREIGN PATENT DOCUMENTS 8210564   12/1983   Japan.

*Primary Examiner*—Tae Yoon
*Attorney, Agent, or Firm*—Renner, Kenner, Greive, Bobak, Taylor & Weber

[57] ABSTRACT

Several methods of using dyes within polymers and specifically in packaging materials are disclosed. These dyes respond to specific stimuli and indicate exposure to stimuli by a change or shift in the frequencies of light which they adsorb. The stimuli include temperature, radiation, chemicals (e.g. $H_2O$, $CO_2$, $NO_2$, ethylene, and $SO_2$), and tensile or compressive stress. Within packaging materials (or affixed thereto as a label, decal or tag) these dyes could indicate spoilage or the possibility of spoilage, that the product has been irradiated, or that the product has been exposed to an undesirably high or low temperature. Many of the shifts in absorption frequencies result in visible color change which a consumer could quickly identify. The tensile or compressive stress sensitive dyes could indicate whether common opposing interlocking polymeric strips used to seal plastic bags have been effectively interlocked to seal the bags.

2 Claims, No Drawings

METHOD OF USING MULTICHROMIC POLYMERS IN PACKAGING

FIELD OF THE INVENTION

This invention relates to the use of photochromic, chemichromic, and piezochromic dyes to indicate specific changes in the environment of the dyes, which dyes respond to specific environment by shifting their light absorption frequencies. One specific field of use is in packaging materials and bags (desirably transparent containers) where the dyes can indicate gases or volatile liquids from contamination or spoilage. Another field of use is frequency specific photochromic dyes in packaging materials which later during use undergo long term color changes to indicate whether the package has or has not been exposed to specific irradiation frequencies. Another field of use is piezochromic dyes which are incorporated into a synthetic polymer to indicate by an absorption of specific light frequencies or alternatively by developing stress whitening to indicate whether stress is present in the polymer.

BACKGROUND

Photochromic dyes are known to undergo reversible color changes on exposure to ultraviolet light. U.S. Pat. Nos. 3,341,330, 3,355,293 and 3,346,385 teach how to form persistent images from thin layers of dyes and how to further treat them with $NO_2$. Similar technology is known in photochromic photography (color photography).

Chemichromic dyes are probably best known by analytical chemists who use pH sensitive dyes to indicate pH and dyes sensitive to specific elements or oxidation states thereof to make calorimetric test methods for determining quantitatively compounds such as iron, amines and lead.

Piezochromic dyes are Compounds which upon exposure to different compressive or tensile forces alter or shift the frequencies of light which they absorb.

SUMMARY OF THE INVENTION

Disclosed are a variety of dyes which can be incorporated into polymeric materials to indicate (by changes in the relative light frequencies which they absorb) the occurrence of an event. The event can be exposure of the dye to a specific irradiation, exposure to a specific chemical, or compressive or tensile forces. These dyes are particularly useful when their shift in light frequency absorption is visibly detectable color change and when used in combination with transparent packaging materials.

DETAILED DESCRIPTION

Dyes known to be photochromic, chemichromic, and piezochromic may be incorporated into polymeric material where they will continue to demonstrate the specific stimuli sensitivity. Some polymers may increase or decrease the sensitivity of the dye while other polymers may cause a shift in the absorbed frequencies of light of the dye. The wavelengths of light desirably absorbed are from about 10 nm to about 1 mm which include ultraviolet, visible and infrared. More desirably, one or more frequencies of absorbed light, which shift on exposure to the stimuli, are in the visible light region which is from about 0.4 µm to about 0.7 µm. Exposure of the dye to its specific stimuli causes a change in the dye which causes a change in the amount of one or more frequencies of light which the dye absorbs. These shifts are usually characterized by a spectrometer which measures the amount of absorbed or reflected light from a material at numerous different frequencies. Many of these dyes after exposure to their specific stimuli undergo a large enough shift in one or more frequencies of visible light absorbed by the dye that the exposure to the stimuli can be detected by a person as a change in the perceived color of the dye. These dyes having visual color changes are preferred for packaging applications and for household use or consumption. Commercial applications of packaging materials might use visible, ultraviolet or infrared color changes as indicators but would require equipment to determine if the dyes had changed their absorption frequencies in only nonvisible wavelengths of light.

A preferred use of these dyes is in packaging materials to indicate the usable condition of the packaged article. Such uses include photochromic dyes which indicate whether a packaged food or medical use product has been partially or fully sterilized by an irradiation process. Photochromic dyes are dyes which undergo a change or shift in the relative amounts of light of specific frequencies which they absorb, when they are exposed to specific frequencies of irradiation. A temporary color change would indicate upon immediate inspection that the irradiation was successfully completed. A more permanent color change would indicate to the final consumer that the packaged article had, in fact, been irradiated and was safe to use.

Chemichromic dyes could function with packaged articles to indicate whether a gas or a volatile liquid was present inside the packaged article. Chemichromic dyes undergo a change, when exposed to specific chemicals (such as $H_2O$, $CO_2$, $NO_2$, ethylene, $SO_2$), in the relative amount of specific frequencies of radiation absorbed. As recited above, for photochromic dyes, this can result in a visually detectable or a detectable by instrument color change. Desirably, the dyes are sensitive to undesirable products (such as moisture in moisture sensitive goods (e.g. electronics) or products of degradation or spoilage of food products (e.g. $CO_2$, ethylene, $SO_2$ in food containers). Thus, one use of the dye is to detect if spoilage of the contained food product is imminent or has already occurred. A label, legend, or decal would be desirably included with the packaged article explaining where the dye was and how to determine if an undesirable product was contained within the package by examining the portion of the packaging containing the dye.

Thermochromic dyes which change the one or more frequencies of light which they principally absorb in response to one or more temperature changes can be used to indicate whether a polymer is currently or has in the past been exposed to a particular temperature. The color change can be a permanent shift in the one or more frequencies absorbed or a reversible shift that slowly or quickly reverts back to absorbing appropriate frequencies for the initial temperature. A reversible shift would be desirable to monitor a process or storage conditions and avoid prolonged exposure to elevated or reduced temperatures. A permanent shift would be desirable to monitor whether a product has since the packaging was installed been exposed to specific elevated or reduced temperature.

Piezochromic dyes would desirably be included in a polymeric material to indicate whether the specific polymeric material was in compressive or tensile stress. In packaging materials, these dyes would be useful as they could identify stressed (tensile or compressive) areas within the package. Holes, tears, and abraded areas could be identified by their different apparent color. Chemical compounds known as sensitizers could optionally be added to the dyes to change or adjust the amount of stress required to trigger an absorption of different light frequencies or cause a color change. Compressive stress could be applied by stacking the articles or other means. One use of absorption changes of piezochromic dyes would be to indicate whether a desired or undesired compressive stress is present in interlockingly engagable polymer strips. These strips are known to consumer and are used to seal many transparent bags. The strips may engage with themselves in some circumstances but usually one strip is used with a longitudinally positioned second strip having an appendage or channel to engage with an appendage or channel of the first strip. A problem with these strips is that it is difficult to visually perceive if they have been securely interlocked to seal the contents of the package. Desirably, the piezochromic dye is included in the polymer of the one or more appendages and/or channel forming material in one or both strips. In the interlocked position of one or more strips, the appendages and channel material would be in compressive or tensile stress. Desirably, the dye would indicate this stressed condition by a change in absorbed light frequencies in the appendages and/or channel material.

A variation of using piezochromic dyes in the stressed portion of interlocking polymer strips is to mold or machine the strips to create dimensional variation in one or more areas in the interlocking strips. These portions of the polymer strips, due to their having one or more areas of increased dimension as compared to adjacent areas (of the appendage or channel), or their having one or more areas of decreased dimension relative to adjacent areas serve as a stress concentrator within the appendage or channel. The dye in areas of stress concentration would thus be able to change its relative light absorption frequencies at a lower total tensile or compressive stress enhancing its sensitivity. With stress whitening polymers the areas of stress concentration may whiten without any dye present indicating that the interlocking strips are interlocked sealing the container and the polymer used in one or more parts of the strip is under compressive or tensile stress.

The above photochromic, chemichromic thermochromic, and piezochromic dyes may undergo temporary or permanent change (shift) in the relative amounts of specific frequencies of light absorbed. For applications where the polymer is to be reused without remolding it, the color changes would be desirably temporary or reversible. In applications where the polymer is used one time before being recycled, desirably the color change is permanent. Specific applications may require reversible, temporary, permanent, and semipermanent changes. The use of temperature changes and/or exposure to chemicals are viable ways of reversing color changes. Thus a polymeric food container could be designed to reverse any color change during the wash or dry cycle within a dishwasher where it would be exposed to elevated temperature and chemicals.

The polymer containing the dye can be processed by a variety of well known polymer processing techniques. These include extrusion, calendering, injection molding, transfer molding, compression molding, solution casting and variations thereof. The dyes may be adsorbed onto or absorbed into polymers. The dyes may be part of a polymer dispersion such as latex, paint, ink, etc. which is coated onto a polymer and dried.

Food products are a preferred material to be contained in the packaging materials of this application. Food includes fruits, vegetables, meats (beef, pork, poultry, fish etc.), cereals, grains, dairy products (cheese butter, milk, sour cream, ice cream) and mixtures or combinations of the above materials and partially or fully cooked versions thereof.

The packaging material anticipated includes natural and synthetic polymers such as paper; waxes; thermoplastic polymers including polyolefins such as polyethylene, poly(vinylidene chloride), polystyrene, foamed polystyrene; thermoset polymers; thermoplastic elastomers; liquid crystal polymers such as Xydar from Amoco, and aromatic liquid crystal polyesters such as 2-naphthalenecarboxylic acid, 6-(acetyloxy)-, polymer with 4(acetyloxy) benzoic acid sold as Vectra™ by Hoechst Celanese Corp.; etc. Preferred packaging materials include at least one transparent component. The packaging material is also known as bags, wraps, films, pads, trays, papers and molded containers or spacers. If desired the dye may be affixed or incorporated into packaging material or the package product may include the dye as a label, decal, legend or coating.

The dye may be the following which are chemichromic and/or photochromic:

benzoindolinospiropyran with one or more substituents selected from alkyls of 1 to 5 carbon atoms optionally with one or more other substituent groups either as part of the alkyl or separately present selected from hydroxyl, hydroxyalkyl, amino, carboxyl, aceto, carboxylate, aryloxy, alkylamino, or mercapto;

polyalkylbenzoindolino spiro naphthoxazines with or without one or more substituents as given above for spiropyrans;

triarylmethane leuco dyes such as malachite green leucocyanide, malachite green leucohydroxide, malachite green leucobisulfite and similar leuco dyes from crystal violet, brilliant green, auramine, etc; and metal dithizonates with mercury, platinum, or palladium as the metal atom with or without substituents as described above for spiropyrams.

The following are additional chemichromic dyes:

dyes indicating acidic pH, dyes indicating basic pH, other indicating dyes and triarylmethane dyes.

Preferred dyes are:

1',3'-dihydro-1',3'3'-trimethyl-6-nitrospiro (2H-1-benzopyran-2,2'-(2H)-indole), crystal violet, cresolphthalein, bromocresol green, methyl red, thymol phthaline, malachite green, alizarin red, phloxine B.

Thermochromic dyes are made by reacting the below thermochromic dye intermediate with organic acids, alcohols, or esters. The shifts in light absorption frequency can be adjusted to specific temperatures by the choice of the one or more organic acids, alcohols, or esters or combinations thereof chosen. The acids can be monoacids, diacids and less desirably polyacids. The alcohols can be monohydric, dihydric and less preferably polyols. The alcohols can include carboxylic acid functionality therein. The esters can have monoester, diester, or polyester functionality along with alcohol or carboxylic acid functionality. The desirable acids, alcohols, and esters are organic and have from about 3 to 35 carbon atoms per molecule and more desirably from 10 to 18 carbon atoms per molecule. They can contain linear aliphatic, cyclic, branched, and aromatic groups therein. Desirably they are free of heteroatoms other than carbon, hydrogen, and oxygen.

The dye intermediates useful for this purpose along with their visually detectable color are:

Thermochromic dyes based on the following thermochromic dye intermediates:

Blue: crystal violet lactone or 3,3-bis(4-dimethylaminophenyl)-6-dimethyl amino phthalide.

Green: Malachite green: spiro(isobenzofuran-1 (3H), 9'-(9H) xanthen)-3-one, 2'-(bisphenylmethyl) amino-6-(diethylamino).

Black: 2-anilino-3-methyl-6-diethyl-amino fluoran.

Yellow (orange): 3-(4-dimethylamino) phenyl-3-(di (4-octyl) phenylamino) t- (3H) -isobenzofuranone.

Pink (Magenta): rosaniline (3,3-bis (4-amino-phenyl)-6-aminophthalide.

Red: 3,3-bis(1-butyl-2-methylindol-3-yl) phthalide.

Piezochromic dyes include:

a. Triaryl imidazole dimers of Bis-2,4,5-triaryl imidazoles having one or more substituents groups selected from aryl groups such as phenyl, p-totyl, pchlorophenyl, p-anisyl

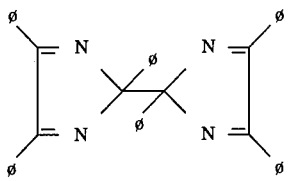

Preferred are: 2, 2', 4, 4' 5, 5'-hexaphenyl bisimidazole;
2, 2', 4, 4' 5, 5'-hexa-p-tolyl bisimidazole;
2, 2', 4, 4' 5, 5'-hexa-p-chlorophenyl bisimidazole;
2, 2'-di -p-chlorophenyl-4, 4', 5, 5'-tetraphenyl bisimidazole;
2, 2'-di-p-Anisyl-4, 4', 5, 5'-tetraphenyl bisimidazole; and
2, 2'-di-p-tolyl-4, 4', 5, 5'-tetraphenyl bisimidazole;

b. Bistetraaryl pyrrole

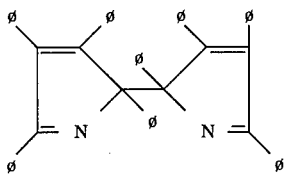

Preferred is: Bistetra phenyl pyrrole c. Bianthrones: Δ10, 10'-bianthrone

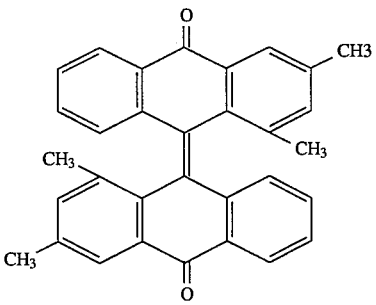

Preferred is: 2, 4, 2', 4'-tetramethyl bianthrone d. Xanthylidene anthrone

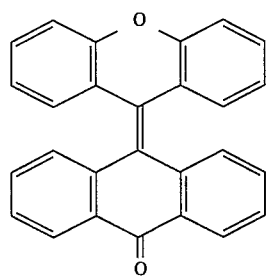

e. Dixanthylene
f. Helianthrone g. Mesonaphthobianthrone

The amount of the above described dyes to be used in polymeric compositions is desirably from 0.001 to 5 wt. % based on the portion of the polymeric composition containing the dye. More desirably the amount is from 0.01 to 5 wt. % and preferably from 0.1 to 1 wt. %. If the polymeric composition includes a non-reactive diluent or solvent that will be removed, the wt. % dye is to be calculated based on the composition less the diluent or solvent.

The above described dyes dispersed in a polymer are useful to indicate either that a particular chemical material is present at one or more specific concentration; that a product has been exposed to one or more particular radiation frequencies; or that a polymer is under compressive or tensile stress; or combinations thereof. The change in the relative absorption of one or more light frequencies indicates whether the stimuli (chemical, radiation, or stress) is present or has occurred.

The following examples illustrate the use of dyes in polymers and their use to detect different stimuli.

EXAMPLE 1

One-tenth of a gram of 6-nitro-1', 3', 3'-trimethylbenzoindolinospiropyran or 6-nitro BIPS is mixed with 100 g of polystyrene commonly known as general purpose polystyrene (GPPS). The mixture is placed in the hopper of a laboratory model injection molding machine. Several 1"×1"×0.1" chips were molded at 400° F. (205° C.). The chips, on cooling, did not have any appreciable coloration. They were clear. These chips were exposed to U.V. light of wavelength 336 nm for 2 sec., 1 min. and 5 min. intervals. The chip exposed for 2 sec. only changed to light purple, which returned to the original shade in 15 minutes. The chip exposed to 1 min. was deeper purple, but it did not return to the original shade for several hours. The chip that was exposed for 5 mins. or more did not return to the original color although the intensity decreased during a period of several days. Although the mechanism of color persistence of overexposed chips is not fully understood, it is explained as follows. On exposure for a few seconds, the first layers of the polymeric chip become partially translucent due to the decreased solubility of the colored form of the photochromic dye in the polymeric substrate allowing only more penetrating, shorter wavelengths of the U.V. light. However, on reaching the inner layers of the polymeric substrate, this effects the coloration. These layers being heat shielded by the outer layers are protected from thermal reversal of the coloration. This can further be promoted by traces of acidic or hydrophilic material incorporated in the photochromic dye or the plastic substrate.

These chips were then suspended in an environmental chamber containing $NO_2$ for 5 minutes. Then they turned yellow and were immersed in hot water for a few seconds. The chips turned red. The intensity of the yellow shade varied; the deeper yellow was obtained from the samples which had longer exposure to U.V. light.

Then some yellow chips were again suspended in the environmental chamber purged with ammonia gas. The chips turned orange to red. The depth and shade of the color depended on the heat and exposure history of the chips.

Both the yellow and red colors on the chips were permanent colors under normal conditions. Thus, three colors were sequentially obtained from a clear chip: from clear to purple, from purple to yellow, and finally from yellow to red.

EXAMPLE 2

Example 1 was repeated using high impact polystyrene (HIPS). This has a hazy white color to begin with, and the final results gave color change from white to purple, from purple to yellow, and from yellow to red under experimental conditions described in example 1.

EXAMPLE 3

One-tenth of a gram of 8-Methoxy-6-nitro BIPS was intimately mixed with PVC plastisol along with a few drops of toluene. The mixture was used to mold circular patties, 2" in diameter and 0.2" in thickness. This was done using aluminum weighing dishes. The plastisol mixture was taken and heated in an oven at about 205° C. for about two minutes. The patties were flexible and blue in color when hot but returned to white color on cooling. When the patty was exposed to U.V. light for a second, it turned deep blue. The color returned in 60 minutes. When the exposure time was increased to five minutes, the return time was extended to several hours, but the coloration was blue. When the exposure to U.V. continued for 90 minutes, the yellow color so formed was permanent. When the U.V. exposure was performed in an atmosphere of an acid vapour such as HCl, the blue coloration that occurred was permanent under ordinary conditions. Thus two colors were obtained from the starting white color without any sequential treatment. That means from white to blue and from white to yellow. The mechanism of the acid environment which prevents the molecular arrangement of the colored form to revert to that of the colorless form is well known. The mechanism of yellow coloration on prolonged exposure to U.V. is attributed to the breakdown of chromophore into nonphotochromic entities.

EXAMPLE 4

One-tenth of a gram of finely divided phthalimide was incorporated in polypropylene homopolymer of melt index 18 by injection molding 1"×1"×0.1" chips. A 1% solution of 6-Nitro BIPS in toluene was made, and it was adsorbed on the phthalimide in the polymer chip which was immersed in the above solution for several minutes. A red color was formed on exposure to U.V. light which was permanent under normal conditions as well as on exposure to visible light. Certain photochromic compounds show negative photochromism and positive thermochromism. A negative photochromism is exhibited by 6-Nitro BIPS under certain conditions: for example, coloration occurred in the absence of light which is erased on exposure to visible light. This is partially explained as a positive thermochromic effect in the dark and a negative photochromic effect in the visible light. The presence of phthalimide in the system prevented the photo erasure.

EXAMPLE 5

High impact polystyrene (1"×1"×0.1") chips containing 0.1% nitro BIPS and 0.01% Rhodamine B lactam were made by injection molding as in example 1. The chip was exposed to U.V. light, it turned bluish purple. On treating it with $SO_2$ gas in an environmental chamber for two minutes, the bluish chip turned yellow, and this yellow color was permanent. On heating the chip gently to effect reaction with Rhodamine B lactam, the final permanent red color was obtained.

While in accordance with the patent statutes the best mode and preferred embodiment has been set forth, the scope of the invention is not limited thereto, but rather by the scope of the attached claims.

What is claimed is:

1. A method of using packaging material to indicate exposure of an article packaged therein to irradiation, comprising:

a) affixing to or incorporating into the packaging material one or more photochromic dyes;

b) preparing a package with said packaging material and said article;

c) after a) and b) exposing the dye to one or more radiation frequencies such that the dye absorbs said one or more radiation frequencies, indicating exposure or lack of exposure of said article to irradiation; and, wherein said photochromic dye is one or more of fulgides, triaryl methane leuco-cyanides, triaryl methane leuco-hydroxides or triaryl methane leucobisulfites.

2. A method according to claim 1, wherein the radiation frequencies absorbed are visible light frequencies facilitating the detection of said irradiation by a visually perceptible color change.

* * * * *